(12) United States Patent
Andres et al.

(10) Patent No.: US 9,833,438 B2
(45) Date of Patent: Dec. 5, 2017

(54) TREATMENT OF ATOPIC DERMATITIS WITH INDIGO NATURALIS OR INDIGO PRODUCING PLANT EXTRACT

(71) Applicant: Galderma S.A., Cham (CH)

(72) Inventors: Philippe Andres, Peymeinade (FR); Laurent Chantalat, Antibes (FR); Yin-Ku Lin, Keelung (TW)

(73) Assignee: Galderma S.A., Cham (CH)

( * ) Notice: Subject to any disclaimer, the term of this patent is extended or adjusted under 35 U.S.C. 154(b) by 0 days.

(21) Appl. No.: 15/634,489

(22) Filed: Jun. 27, 2017

(65) Prior Publication Data

US 2017/0290804 A1 Oct. 12, 2017

Related U.S. Application Data

(63) Continuation of application No. PCT/EP2016/057769, filed on Apr. 8, 2016.

(30) Foreign Application Priority Data

Apr. 9, 2015 (EP) .................................... 15163067

(51) Int. Cl.
| | | |
|---|---|---|
| *A61K 36/00* | (2006.01) | |
| *A61K 31/404* | (2006.01) | |
| *A61K 36/70* | (2006.01) | |
| *A61K 31/519* | (2006.01) | |
| *A61K 9/16* | (2006.01) | |
| *A61K 9/00* | (2006.01) | |
| *A61K 45/06* | (2006.01) | |

(52) U.S. Cl.
CPC .......... *A61K 31/404* (2013.01); *A61K 9/0014* (2013.01); *A61K 9/16* (2013.01); *A61K 31/519* (2013.01); *A61K 36/70* (2013.01); *A61K 45/06* (2013.01); *A61K 2236/33* (2013.01); *A61K 2236/51* (2013.01); *A61K 2236/53* (2013.01)

(58) Field of Classification Search
CPC ...................................................... A61K 36/00
See application file for complete search history.

(56) References Cited

U.S. PATENT DOCUMENTS

| | | |
|---|---|---|
| 2010/0034757 A1 | 2/2010 | Fujii et al. |
| 2012/0213868 A1 | 8/2012 | Lin |
| 2013/0331400 A1 | 12/2013 | Kusakari et al. |
| 2014/0243354 A1 | 8/2014 | Chantalat et al. |

FOREIGN PATENT DOCUMENTS

| | | |
|---|---|---|
| CN | 1317322 A | 10/2001 |
| EP | 0987027 A1 | 3/2000 |
| EP | 1495762 A1 | 1/2005 |
| EP | 1495764 A1 | 1/2005 |
| EP | 2489358 A1 | 8/2012 |
| JP | 2006-241080 A | 9/2006 |
| KR | 2005-077310 A | 8/2005 |
| KR | 2013-0071857 A | 7/2013 |
| WO | 2014118040 A1 | 8/2014 |

OTHER PUBLICATIONS

Int'l Search Report and Written Opinion dated Jun. 21, 2016 in Int'l Application No. PCT/EP2016/057769.
Han et al., "Genuine traditional Korean medicine, Naju Jjok (Chung-Dae Polygonum tinctorium) improves 2,4-dinitrofluorobenzene-induced atopic dermatitis-like lesional skin," Phytomedicine, vol. 24, pp. 453-460 (2014).
Han et al, "Tryptanthrin ameliorates atopic dermatitis through down-regulation of TSLP," Archives of Biochemistry and Biophysics, vol. 542, pp. 14-20 (2013).
Int'l Search Report and Written Opinion dated Jun. 20, 2016 in Int'l Application No. PCT/EP2016/057761.
Int'l Search Report and Written Opinion dated Jun. 20, 2016 in Int'l Application No. PCT/EP2016/057763.
Chiang, "An in Vitro Study of the Antimicrobial Effects of Indigo Naturalis Prepared from Strobilanthes Formosanus Moore", Molecules, vol. 18, No. 11, pp. 14381-96 (Nov. 21, 2013).

*Primary Examiner* — Qiuwen Mi
(74) *Attorney, Agent, or Firm* — Panitch Schwarze Belisario & Nadel LLP

(57) ABSTRACT

A pharmaceutical or cosmetic composition comprising an Indigo Naturalis or Indigo-producing plant extract for treating atopic dermatitis and any form of eczema, and a method of treating atopic dermatitis comprising administering a therapeutically effective amount of an Indigo Naturalis or Indigo-producing plant extract to a subject in need thereof are described.

20 Claims, 7 Drawing Sheets

A

B

TREATMENT OF ATOPIC DERMATITIS WITH INDIGO NATURALIS OR INDIGO PRODUCING PLANT EXTRACT

CROSS-REFERENCE TO RELATED APPLICATION

This application claims the benefit, under 35 U.S.C. §365 of International Application PCT/EP2016/057769 filed Apr. 8, 2016, which was published in the English language on Oct. 13, 2016, under International Publication No. WO/2016/162488 A1, and which claims the benefit of European patent application No. 15163067.0, filed Apr. 9, 2015, the disclosure of each of which is hereby incorporated by reference herein in its entirety.

TECHNICAL FIELD

This application relates to a use of an Indigo Naturalis or an Indigo-producing plant extract, in particular a use for treating atopic dermatitis and any form of eczema.

BACKGROUND

Atopic dermatitis (AD) is a common, chronic, relapsing skin disease related to inflammatory dermatologic changes that are clinically characterized by pruritus and erythematosus patches and plaques with a typical morphology and distribution. See Hanifin J M. *Diagnostic features of atopic dermatitis.* Acta Derm Venereol 1980; 92(*Suppl*): 44-7. The disease manifests during infancy for most patients with AD, and the reported prevalence among children is 17% to 20% (See Levy R M, Gelfand J M, Yan A C. *The epidemiology of atopic dermatitis.* Clin Dermatol 2003; 21(2): 109-15). Adults are also affected by AD (from 2 to 10% of adults).

Approximately 60% AD subjects experience eruptions in the first year of life and 90% by five years of age. AD may follow a relapsing course and can be characterized by episodes of intense pruritus, lichenification, and severely dry skin as well as being susceptible to cutaneous infection. AD is often associated with elevated serum immunoglobulin (IgE) levels and/or a personal or family history of related atopic disorders, such as atopic dermatitis, allergic rhinitis or asthma. The most common therapy for controlling AD is corticosteroid treatment; however, these therapies are not completely effective for all patients. In addition, there are concerns about side effects, especially in children, which had led patients and families to seek complementary and/or alternative treatments.

There is thus a need to develop alternative medications for treating atopic dermatitis.

SUMMARY

It has been discovered that Indigo Naturalis or Indigo-producing plant extract is particularly efficient for the treatment of atopic dermatitis, more specifically for the topical treatment of atopic dermatitis and any form of eczema.

This application relates to an Indigo Naturalis or Indigo-producing plant extract that is effective for treating atopic dermatitis. Indigo Naturalis or Indigo-producing plant extract can be used as the sole therapy for the treatment of atopic dermatitis.

In one aspect, this application provides a pharmaceutical or cosmetic composition comprising an Indigo Naturalis or Indigo-producing plant extract for treating atopic dermatitis.

The extract may comprise indirubin in an amount of at least 65% w/w of the extract, for example, 65%-90% w/w of the extract. It may further comprise indigo in an amount of 0.1%-15% w/w of the extract, and in another further embodiment, the extract may also comprise indigo in an amount of 0.1%45% w/w of the extract and tryptanthrin and/or qingdainone each in an amount of 0.1-5% w/w of the extract.

As mentioned above, the treatment of atopic dermatitis with Indigo Naturalis or Indigo-producing plant extract is particularly effective so that the treated subject may not require any other standard therapy, such as a corticoid or calcineurin inhibitor therapy.

In another aspect, the invention provides use of an Indigo Naturalis or Indigo-producing plant extract in the preparation of a medicament for treating atopic dermatitis.

In further another aspect, the invention provides an Indigo Naturalis or Indigo-producing plant extract for treating atopic dermatitis.

In still another aspect, the invention provides a method of treating atopic dermatitis comprising administering a therapeutically effective amount of an Indigo Naturalis or Indigo-producing plant extract to a subject (e.g., human) in need thereof.

The Indigo Naturalis or Indigo-producing plant extract includes any extract obtained from an Indigo Naturalis or an Indigo-producing or an Indigo-bearing plant as starting material.

DETAILED DESCRIPTION

Figure 1:
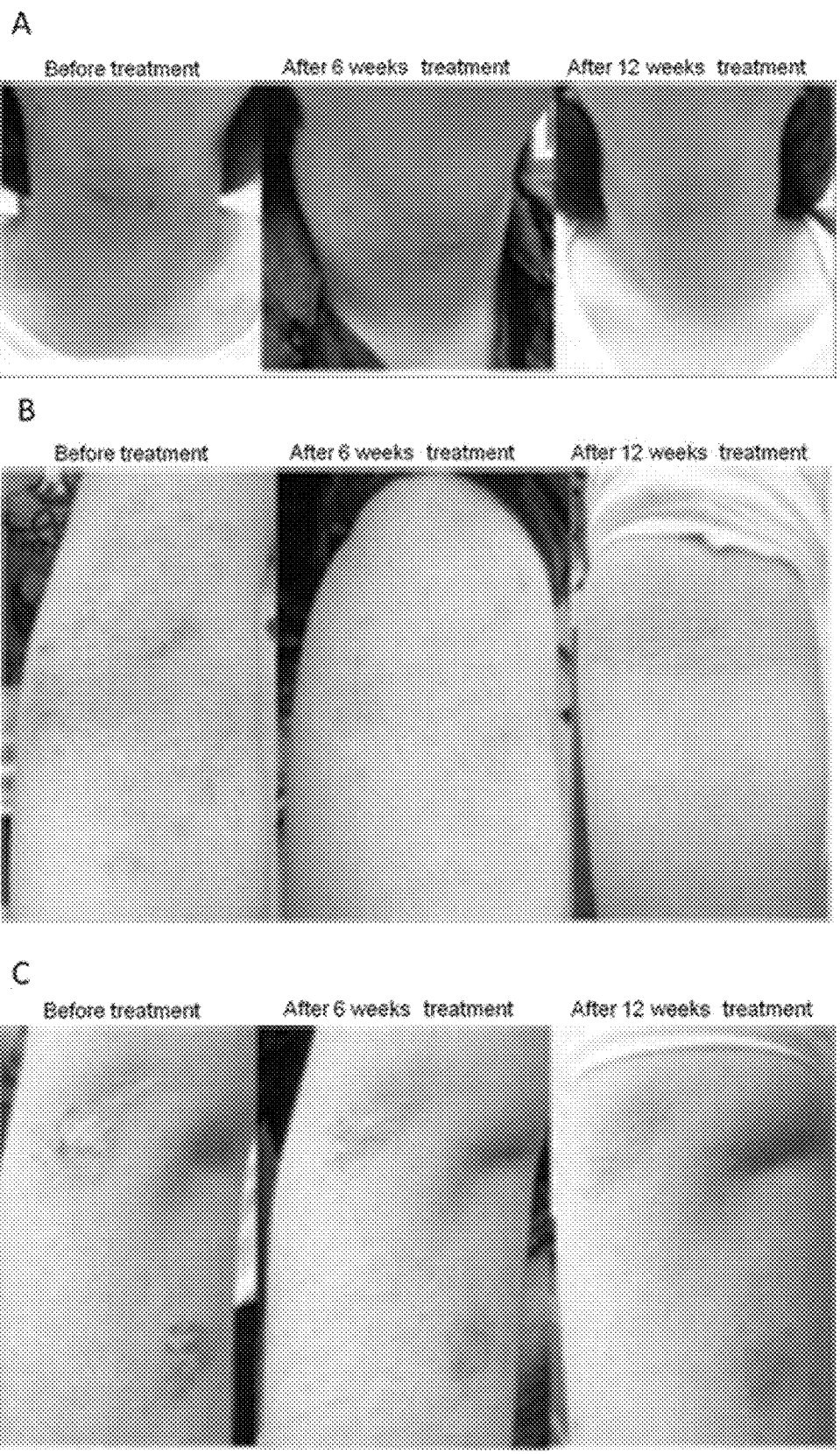
FIG. 1 Patient A—example 16—clinical improvement on the appearance of skin lesions after treatment with Indigo Naturalis extract ointment, as described in Example 10. Photos of the neck (A), left arm antecubital fossae (B) and left forearm (C) taken at baseline, week 6 and week 12.

It is to be understood that, if any prior art publication is referred to herein, such reference does not constitute an admission that the publication forms a part of the common general knowledge in the art.

Indigo Naturalis, also known as Qingdai, is obtained from one or more Indigo bearing plants including *Indigofera tinctoria* L., *Baphicacanthus cusia* (Nees) *Bremek* (syn. *Strobilanthes cusia* (Nees)), *Persicaria tinctoria* (Aiton) *Spach*. (syn. *Polygonum tinctorium* Aiton, *P. tinctorium* Lour.) and *Isatis tinctoria* L. (syn. *Isatis indigotica* Fort.) and/or *Strobilanthes Formosanus*. It may come from the whole plant or at least one part thereof, such as from the plant leaves and/or stems. After harvest and collection, it may be processed by fermentation, for example. Indigo Naturalis is usually a dark-blue powder.

An Indigo-producing plant extract, as used herein, refers to an extract from Indigo Naturalis or from the leaves and/or stems (or a part thereof) of one or more Indigo-bearing plant or Indigo-producing plant, where the extraction may be performed by using one or more organic solvents, one or more non-organic solvents, or a combination thereof. The extract may include at least one enriched ingredient (having a higher w/w percentage than that existing in Indigo Naturalis) such as tryptanthrin, isatin, indirubin, indigo, or qingdainone. The extract may be a solid, liquid, or any form in-between (e.g., semi-solid). An Indigo-producing plant extract preferably refers to an extract from Indigo Naturalis.

In a particular embodiment, the Indigo Naturalis or Indigo-producing plant extract is enriched in indirubin, for example the extract may contain indirubin in an amount of at least 65% w/w of the extract, for example, 65%-90% w/w of the extract. The extract may further contain indigo in an amount of 0.1%-15% w/w of the extract. The extract may also contain tryptanthrin and/or qingdainone each in an amount of 0.1-5% w/w.

One example of the Indigo Naturalis or Indigo-producing plant extract is an ethyl acetate extract (EA-extract), which may be prepared as illustrated by Example 2 in this application. The content of each ingredient in the extract may vary. As an example, the extract may contain indirubin in an amount of at least 65% w/w of the extract, for example, 65%-90% w/w of the extract. The extract may further contain indigo in an amount of 0.1%-15% w/w of the extract. The extract may also contain tryptanthrin and/or qingdainone each in an amount of 0.1-5% w/w.

A further example of Indigo Naturalis extract is an oil extract, particularly an olive oil extract. An oil extract can be prepared by the method disclosed in U.S. Pat. No. 8,784, 905. More specifically, the oil extract of Indigo Naturalis is an oil-extracted product of Indigo Naturalis which is obtained by a process comprising extracting Indigo Naturalis powder with an oil under heating, optionally followed by a refining treatment by filtration. More preferably, in said process, the oil-extracted product is obtained after the refining treatment has a decreased indigo content. In said process, extracting indigo naturalis powder is more particularly conducted at an elevated temperature not higher than 155° C., and preferably conducted at a temperature ranging from 100° C. to 155° C. The oil used in said process is preferably selected from the group consisting of vegetable oils, animal oils, mineral oils, and combinations thereof. More preferably, the oil is a vegetable oil and can be selected from the group consisting of olive oil, cottonseed oil, sesame oil, sunflower seed oil, peanut oil, wheat germ oil, soybean oil, jojoba oil, evening primrose oil, coconut oil, palm oil, sweet almond oil, aloe oil, apricot kernel oil, avocado oil, borage oil, hemp seed oil, macadamia nut oil, rose hip oil, pecan oil, hazelnut oil, sasanqua oil, rice bran oil, shea butter, corn oil, *camellia* oil, grape seed oil, canola oil, castor oil, and combinations thereof. The content of each ingredient in the oil extract may vary. As an example, the extract may contain indirubin in an amount of at least 65% w/w of the total amount of extracted alkaloids, for example, 65%-90% w/w of the total amount of extracted alkaloids. The extract may further contain indigo in an amount of 0.1%-15% w/w of the total amount of extracted alkaloids. The extract may also contain tryptanthrin and/or qingdainone each in an amount of 0.1-5% w/w of the total amount of extracted alkaloids.

Another example of Indigo Naturalis or Indigo-producing plant extract is an extract prepared by a process comprising the following steps:
  a) an extraction step: extracting Indigo Naturalis or the leaves and/or stems of one or more Indigo-bearing plant or Indigo-producing plant, preferably selected from the group consisting of *Indigofera tinctoria* L., *Baphicacanthus cusia* (Nees) *Bremek* (syn. *Strobilanthes cusia* (Nees)), *Persicaria tinctoria* (Aiton) *Spach*. (syn. *Polygonum tinctorium* Aiton, *P. tinctorium* Lour.) and *Isatis tinctoria* L. (syn. *Isatis indigotica* Fort.) and/or *Strobilanthes Formosanus*, with a first polar solvent or moderately polar solvent to obtain a mixture of extraction;
  b) a filtration step: filtering the mixture of extraction to obtain a filtrate;
  c) a concentration step: concentrating the filtrate to obtain a crude extract;
  d) a washing step: washing the crude extract with a non-polar solvent, and optionally a second polar solvent, to obtain a washing mixture; and
  e) a filtration step: filtering the washing mixture to obtain a refined extract optionally after a drying step, for example, according to a conventional method for drying.

In a particular embodiment, a crude extract obtained from the concentration step c) is subjected to the following procedure for at least one cycle till obtaining a refined extract: the crude extract is washed by a solvent (step d), and filtered (step e) to yield a refined extract, optionally followed by a drying step. According to a specific embodiment, the washing step d) and filtration step e) are performed by only one cycle to obtain the refined extract. When more than one cycle is applied, the same or different solvents for washing can be used. Further, the crude extract can be washed with a solvent under reflux, the mixture can be cooled to room temperature and then filtered to yield a refined extract, optionally followed by a drying step.

In a preferred embodiment, two cycles are performed. Particularly, the crude extract obtained by the concentration step c) is washed in a non-polar solvent, preferably hexane (step d) and filtered (step e), optionally followed by a drying step. The hexane extract is then washed by an organic polar solvent, preferably ethanol (step d) and then filtered (step e) to obtain a refined extract, optionally followed by a drying step.

Optionally, a micronization step is performed after step e), providing thereby a refined extract having a particle size between 25 and 35 μm, preferably of about 30 μm.

In a preferred embodiment, a refined extract may be prepared by a process comprising the following steps consisting of: a) (i) adding an extracting solvent, a polar or moderately polar solvent (such as an alcohol or ethyl acetate), to Indigo Naturalis powder to yield a mixture; (ii) heating and stirring the mixture for a period of time (e.g., 30 min, 1 hour, 2 hours); b) (iii) filtering the heated mixture while hot to remove insoluble by-products to yield a filtrate; c) (iv) concentrating the filtrate to yield a crude extract; d) (v) adding a washing solvent (for example, water a non-polar and/or a polar solvent or a mixture thereof) to the crude extract to yield a washing mixture; (vi) heating and stirring the washing mixture for a period of time (e.g., 30 min, 1 hour, 2 hours); e) (vii) filtering the washing mixture, for example at room temperature (e.g. 18-35° C.) to collect a refined extract; optionally (viii) repeating steps (v) to (vii) until the amount of indirubin (% w/w) in the refined extract is more than 55% (w/w), preferably more than 65% (w/w) as measured by HPLC method, and optionally (ix) drying the residue according to a conventional method (e.g., air-drying, lyophilization) to obtain a dried extract. The washing solvent in steps (v) and (viii) can be the same or different.

In a more preferred embodiment, a refined extract is prepared by a process comprising the steps of:
  a) extracting Indigo Naturalis with ethanol at reflux between 2 and 8 hours,
  b) filtering the mixture at a temperature not less than 65° C. to obtain a filtrate,
  c) concentrating the filtrate, to obtain a crude extract, said crude extract is optionally filtered (with addition of water) in order to remove completely the solvent and the last components still present in the solvent and dried,
  d) (i) washing the crude extract with hexane at a temperature not less than 50° C. between 15 and 60 min,
    (ii) filtering at room temperature the mixture obtained at step d) (i) to obtain a product, optionally rinsing it with ethanol and water
    (iii) washing the product obtained at step d) (ii) with ethanol at reflux, and
  e) filtering at room temperature the washing mixture obtained at step d) and drying the resulting product at a temperature less than 80° C. to obtain an extract which is optionally micronized.

In another preferred embodiment, when the refined extract is micronized in the last step, the particle size is around 99% in the range 25 to 35 μm, preferably of about 30 μm.

As used herein, "about" or "around" will be understood by a person of ordinary skill in the art and will vary to some extent on the context in which it is used. If there are uses of the term which are not clear to persons of ordinary skill in the art given the context in which it is used, "about" or "around" will mean up to plus or minus 20%, preferably 10% of the particular term.

The term "refined extract", as used herein, refers to a solid, semi-solid or oily extract which contains less than 10% (w/w) of water and/or solvents used in the process for preparing the said refined extract. A refined extract is more preferably characterized by an increase amount of active ingredients, including alkaloids among which indigo, indirubin, tryptanthrin, and/or qingdainone are present, preferably enriched in indirubin, compared to Qingdai or Indigo Naturalis. More specifically, the refined extract according to the invention comprises at least 60%, or more preferably more than 65%, (w/w) of active ingredients, including indigo, indirubin, tryptanthrin, and/or qingdainone.

The term "crude extract", as used herein, refers to a solid, semi-solid or oily extract which contains less than 15% (w/w) (e.g., 5-15%, 5-10%) of water and/or solvents used in the process for preparing the refined extract. The crude extract is less enriched in indirubin, than the refined extract as compared to Qingdai or Indigo Naturalis. The crude extract is obtained by the concentration step c) according to the invention. The concentration step is more particularly carried out by sending the filtrate to a concentrator (for instance at reduced pressure), as to remove water and/or solvents used in the process and concentrating thereby the active ingredients present in the extract, including indigo, indirubin, tryptanthrin, and/or qingdainone.

"one cycle", as used herein, refers to the two steps of the washing step d) and filtration step e) which are performed sequentially once. "two cycles", as used herein, refers to the two steps of the washing step d) and filtration step e) which are performed sequentially twice.

According to a specific embodiment, the Indigo Naturalis or Indigo-producing plant extract according to the invention is an oil extract as defined above or an extract of Indigo Naturalis or Indigo-producing plant obtained by the process as above detailed comprising steps (a)-(e), optionally including one of the above described specific embodiments.

A therapeutically effective amount, as used herein, refers to a dose level of an Indigo Naturalis or Indigo-producing plant extract that yields a therapeutic benefit (for example, amelioration, alleviation or cure of the diseases, disorder or symptoms of atopic dermatitis) to a patient on average.

The invention also provides a composition for treating atopic dermatitis containing an Indigo Naturalis or Indigo-producing plant extract. According to a specific embodiment, the composition comprises an Indigo Naturalis or Indigo-producing plant extract as the sole active ingredient. The Indigo Naturalis or Indigo-producing plant extract may be used directly without further formulation, or included in a pharmaceutical or cosmetic composition that comprises the extract.

The extract may comprise indirubin in an amount of at least 65% w/w of the extract, for example, 65%-90% w/w of the extract. It may further comprise indigo in an amount of 0.1%-15% w/w of the extract, and in another further embodiment, the extract may also comprise indigo in an amount of 0.1%-15% w/w of the extract and tryptanthrin and/or qingdainone each in an amount of 0.1-5% w/w.

The compositions, methods or uses of the invention may be used alone (i.e., in replacement of current treatments) or in combination with current treatments (e.g., corticoids or calcineurin inhibitors or phosphodiesterase inhibitors (PDE4/PDE7)), to improve their efficacy.

In an embodiment, Indigo Naturalis or Indigo-producing plant extract is used as the sole active ingredient (e.g. as a single therapy). According to this embodiment, the composition preferably comprises an Indigo Naturalis or Indigo producing plant extract as the sole active ingredient.

In another embodiment, the Indigo Naturalis or Indigo-producing plant extract can be used in combination with at least one other therapy, such as with at least one corticoid or calcineurin inhibitor.

In one embodiment, the method and use of the invention can also comprise a corticosteroid, a calcineurin inhibitor or a phosphodiesterase inhibitor in combination with the Indigo Naturalis or Indigo-producing plant extract.

In one embodiment, the composition as described above can also comprise a corticosteroid, calcineurin inhibitor or a phosphodiesterase inhibitors in combination with the Indigo Naturalis or Indigo-producing plant extract.

The corticosteroids according to the present application include, but are not limited to, mometasone, fluticasone, clobetasone, hydrocortisone, hydroxyltriamcinolone, alpha-methyl dexamethasone, dexamethasone-phosphate, beclomethasone dipropionate, alclometasone, clobetasol valerate, clobetasol dipropionate desoximetasone, diflorasone, fluociriolone, fluocinonide, halobetasol, desonide, desoxycorticosterone acetate, dexamethasone, dichlorisone, deflorasonediacetate, diflucortolone valerate, fluadronolone, fluclarolone acetonide, fludrocortisone, flumethasone pivalate, fluosinolone acetonide, fluocionide, flucortine butylester, fluocortolone, flupredidene (flupredylidene) acetate, flurandronolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenalone acetonide, medrysone, amciafel, amcinafide, betamethasone and its esters, chlorprednispne acetate, clocortelone, clescinolone, dichlorisone, difluprednate, flucloronide, flunisolide, fluoromethalone, fluperolone, fluprednisolone, hydrocortisone valerate, hydrocortisone cyclopentylpropionate, hydrocortamate, meprednisone paramethasone, prednisolone, prednisone, beclomethasone, triamcinolone and the mixtures thereof.

The calcineurin inhibitors according to the present application include, but are not limited to, tacrolimus or pimecrolimus.

The pharmaceutical composition of the invention may be formulated into a suitable dosage form for topical or oral administration using technology well known to those skilled in the art. The pharmaceutical composition can additionally comprise a pharmaceutically acceptable carrier such as those widely employed in the art of drug-manufacturing. For instance, the pharmaceutically acceptable carrier may include one or more of the following agents: solvents such as olive oil, olive oil refined, cottonseed oil, sesame oil, sunflower seed oil, peanut oil, wheat germ oil, soybean oil, jojoba oil, evening primrose oil, coconut oil, palm oil, sweet almond oil, aloe oil, apricot kernel oil, avocado oil, borage oil, hemp seed oil, macadamia nut oil, rose hip oil, pecan oil, hazelnut oil, sasanqua oil, rice bran oil, shea butter, corn oil, *camellia* oil, grape seed oil, canola oil, castor oil, and combinations thereof, preferably olive oil refined, emulsifiers, suspending agents, decomposers, binding agents, excipients, stabilizing agents, chelating agents, diluents, gelling agents, thickening agent such as beeswax and/or petroleum jelly, preservatives, lubricants, absorption delaying agents, liposomes antioxidants such as butylhydroxytoluene or butylhydroxyanisole, and the like. A topical formulation suitable for the pharmaceutical composition may be an emulsion, a gel, an ointment, a cream, a patch, an embrocation, an aerosol, a spray, a lotion, a serum, a paste, a foam, or a drop. In some embodiments, the pharmaceutical composition is formulated into an external preparation by admixing the extract according to this application with a base such as those that are well known and commonly used in the art.

According to a specific embodiment, the compositions, methods or uses of the invention are suitable for a topical treatment of atopic dermatitis.

In some embodiments, the dosage and the frequency of administration of the pharmaceutical composition according to this application may vary depending on the following factors: the severity of the disease to be treated, the route of administration, and the weight, age, physical condition and response of the subject to be treated. In further or additional embodiments, the amount of the extract is administered in the range of about 0.001 to about 1000 mg/kg body weight/day, for example, about 0.01 to about 500, 300, or 100 mg/kg body weight/day. In further or additional embodiments, administration can be performed daily or even several times per day, if necessary. By way of examples, the extract of the invention can be administered once, twice, three, four, five or six times a week or more, or once, twice, three or four times a day or more. Duration of the treatment may vary and depends on the severity of the subject. It may last for instance from one week to several months (such as from 2, 3, 4, 5, 6 or 7 weeks to 12, 18, 24, 30, or 36 weeks).

The present invention also provides a cosmetic composition comprising the extract. The composition may be present in a form adapted for topical application comprising a cosmetically or dermatologically acceptable carrier or medium. "Cosmetically or dermatologically acceptable" means media which are suitable for a use in which they come into contact with the skin or human skin appendages without posing a risk of toxicity, intolerance, instability, allergic reaction, etc. In the cosmetic composition, the extract may be previously solubilized in one or more cosmetically or dermatologically acceptable solvents, such as water, glycerol, ethanol, propylene glycol, butylene glycol, dipropylene glycol, ethoxylated or propoxylated diglycols, cyclic polyols, petroleum jelly, a vegetable oil or any mixture of these solvents.

The composition according to the invention may contain 0.001-10 mg, for example 0.01-1 mg of one or more active ingredients per 1 g composition.

The present invention also provides a method of treating atopic dermatitis comprising administering a therapeutically effective amount of an Indigo Naturalis or Indigo-producing plant extract to a subject in need thereof. The extract and compositions above can be used in the treatment or alleviation of a disease or condition. By treatment it is meant at least an alleviation of the symptoms associated with the pathological condition afflicting the subject, where alleviation is used in a broad sense to refer to at least a reduction in the magnitude of a parameter, e.g. symptom, associated with the pathological condition being treated. As such, treatment also includes situations where the pathological condition, or at least symptoms associated therewith, are completely inhibited, e.g., prevented from happening, or stopped, e.g., terminated, such that the host no longer suffers from the pathological condition, or at least the symptoms that characterize the pathological condition. As such, treatment includes both curing and managing a disease condition. Accordingly, the extract and compositions above can be used in the treatment or alleviation of atopic dermatitis.

The efficacy of the extract and compositions can be evaluated by in vivo models with respect to their activities in treating diseases or disorders, for example, clinically trials on humans.

The subject in need of AD treatment according to the invention is any mammal, including a human or a non-human mammal, preferably a human mammal. The subject's age can vary in a wide range, e.g. from 2 months to 80 years old, preferably from 2 to 60. According to an embodiment, the subject is a child, for instance from 2 months to 19 years old, preferably from 2 years to 19 years old. According to another embodiment, the subject is an adult, for instance from 20 to 60 years old. The subject in need of such treatment is affected by atopic dermatitis or is susceptible to develop atopic dermatitis. A subject susceptible to develop atopic dermatitis is a subject with personal or family history of related atopic disorders, such as atopic dermatitis, allergic rhinitis or asthma. According to an embodiment, the subject has been diagnosed with atopic dermatitis, for instance because of an elevated serum immunoglobulin (IgE) levels, and preferably because he meets the diagnostic criteria of Williams et al (Williams H C, Burney P G J, Pembroke A C, Hay R J. The U.K. Working Party's Diagnostic Criteria for Atopic Dermatitis. III. Independent hospital validation. Br J Dermatol 1994; 131:406-16).

Within the context of the invention, the term treatment denotes curative, symptomatic, and preventive treatment. Compositions of the invention can be used in a mammal with existing atopic dermatitis symptoms, such as eczematous lesions, erythema, palpulation/induration, oozing/crusting, pruritus, lichenification, dry skin, or scaly patches on skin. Such symptoms or skin lesions may appear on the scalp, forehead, neck, face, cheeks, arms and/or legs. Atopic dermatitis can be itchy. Mammals and more specifically children may rub or scratch their skin to relieve the itch so that it can lead to a skin infection. Such cutaneous infection can be cured or preferably prevented by such treatment. The skin lesions of AD subjects, such as erythema, palpulation/ induration, oozing/crusting, pruritus, lichenification, or dry or scaly skin, to be treated can be mild, moderate, severe or very severe. Efficacy of the Indigo Naturalis or Indigo-producing plant extract of the invention in treating AD can be assessed by measuring the change from baseline using the Eczema Area and Severity Index (EASI) (Hanifin J M, Thurston M, Omoto M, et al. The eczema area and severity index (EASI): assessment of reliability in atopic dermatitis. EASI Evaluator Group. *Exp Dermatol* 2001; 10(1): 11-8), Body Surface Area (BSA) involved with AD (Hettiaratchy S, Papini R. Initial management of a major burn: II—assessment and resuscitation. BMJ. 2004; 329(7457):101-3), Investigator's Global Assessment (IGA) (Eichenfield L F, Lucky A W, Boguniewicz M, Langley R G, Cherill R, et al. Safety and efficacy of pimecrolimus (ASM 981) cream 1% in the treatment of mild and moderate atopic dermatitis in children and adolescents. *J Am Acad Dermatol.* 2002; 46(4): 495-504), and/or pruritus Numeric Rating Scale (NRS) (Phan N Q, Blome C, Fritz F, et al. Assessment of pruritus intensity: prospective study on validity and reliability of the visual analogue scale, numerical rating scale and verbal rating scale in 471 patients chronic pruritus. *Acta Derm Venereol* 2012; 92: 502-07). In particular, assessments such as IGA and NRS are as described in the examples.

The compositions of the invention will not necessarily cure the patient who has atopic dermatitis but will diminish in a satisfactory manner delaying or slowing thereby the progression or preventing thereby complications of atopic dermatitis. This will ameliorate consequently the patients' skin condition. The compositions of the invention can also be administered to those who do not have atopic dermatitis yet but who would normally develop atopic dermatitis or be at increased risk for said disease, they will not develop said disease. Treatment also includes delaying the development of atopic dermatitis in an individual who will ultimately develop said disease or would be at risk for the disease due to age, familial history, or genetic abnormalities. By delaying the onset of atopic dermatitis, compositions of the invention have prevented the individual from getting atopic dermatitis during the period in which the individual would normally have gotten atopic dermatitis or reduce the rate of development of atopic dermatitis or some of its symptoms.

The novel features of the invention are set forth with particularity in the appended claims. A better understanding of the features and advantages of the present application will be obtained by reference to the following detailed description that sets forth illustrative embodiments.

While embodiments of the present invention have been shown and described herein such embodiments are provided by way of example only. It should be understood that the above described embodiments may be combined if compatible and various alternatives to the embodiments of the invention described herein may be employed in practicing the invention. Those ordinary skilled in the art will appreciate that numerous variations, changes, and substitutions are possible without departing from the invention. It is intended that the following claims define the scope of aspects of the invention and that methods and structures within the scope of these claims and their equivalents be covered thereby.

It is to be understood that, if any prior art publication is referred to herein, such reference does not constitute an admission that the publication forms a part of the common general knowledge in the art. All documents, or portions of documents, cited herein including, without limitation, patents, patent applications, articles, books, manuals, and treatises are hereby expressly incorporated by reference in their entirety for any purpose.

The percentage herein is expressed by weight relative to the weight of the extract, unless otherwise specified.

Further aspects and advantages of the invention will be disclosed in the following illustrative experimental section.

EXAMPLES

A. Preparation of Indigo Naturalis and Indigo Naturalis or Plants Extracts

Example 1—Preparation of Indigo Naturalis

*Strobilanthes formosanus* was harvested in Sansia, New Taipei City, Taiwan. The harvested leaves of *S. formosanus* were immersed in water for several days until the leaves were decomposed by microbial activities. After that, lime was added to the suspension to precipitate Indigo Naturalis.

Example 2—Preparation of Indigo Naturalis and Indigo-Producing Plant Extracts: Ethyl Acetate (EA) Extracts of *S. formosanus* and Indigo Naturalis The leaves of *S. formosanus* were dried in an oven (40° C.) for three days. Twenty-five g of the dried *S. formosanus* leaves were extracted with 300 mL of EA at 40° C. for one hour. Indigo Naturalis (25 g) was also extracted by the same procedure. The EA-extractable compounds of the two samples were then separated from the residue by centrifugation (12,000×g, 20 min) at 15° C. The supernatant was recovered and evaporated to dryness under reduced pressure and stored at −20° C. for bioassays.

Example 3—Preparation of a Refined Indigo Naturalis Extract

Qingdai as used in the following preparation is obtained from Delong Pharmaceutical (Indigo 2.62% and Indirubin 0.284%)

500 g of Qingdai were suspended in 10 L ethyl acetate. The mixture was stirred in reflux for two hours, and then filtered at 75° C. The filtrate was concentrated at reduced pressure to yield a dark solid. The crude extract was stirred in 250 mL hexane and heated to reflux for one hour. After cooling to room temperature, the suspension was filtered to give a dark residue.

0.50 g of the dark residue were refluxed in 25 mL hexane again for one hour, and cooled to room temperature, followed by filtration to give a refined extract as a dark red solid 452 mg. HPLC: 62.9% indirubin, 12.9% indigo, and 0.53% tryptanthrin.

Example 4: Preparation of a Refined Indigo Naturalis Extract 500 g of Qingdai as described in Example 3 were suspended in 10 L alcohol (ethanol). The mixture was stirred in reflux for two hours, and then filtered at 75° C. The filtrate was concentrated at reduced pressure to yield a dark solid, which was stirred in 260 mL hexane and heated to reflux for one hour. Upon cooling to room temperature, the suspension was filtered to give a dark residue.

0.80 g of the dark residue were refluxed in 24 mL alcohol (ethanol) for an additional hour, and then cooled to room temperature, followed by filtration to give a refined extract as a dark red solid (538 mg). HPLC: 83.6% indirubin, 6.35% indigo, and 0.75% tryptanthrin.

Example 5: Preparation of a Refined Indigo Naturalis Extract 500 g of Qingdai as described in Example 3 were suspended in 10 L ethyl acetate. The mixture was stirred in reflux for two hours, and then filtered while hot. The filtrate was concentrated at reduced pressure to yield a dark solid. The crude extract was stirred in 250 mL hexane and heated to reflux for one hour. After cooling to room temperature, the suspension was filtered to give a dark residue.

0.75 g of the dark residue were refluxed in 22.5 mL ethanol for one hour, and cooled to room temperature, followed by filtration to give a refined extract as a dark red solid (538 mg). HPLC: 77.9% indirubin, 15.9% indigo, and 0.56% tryptanthrin.

Example 6: Preparation of a Refined Indigo Naturalis Extract 500 g of Qingdai as described in Example 3 were suspended in 2.1 L DMF. The mixture was stirred at 50° C. for 40 minutes. Upon cooling to 20° C., the suspension was filtered. The filtrate was concentrated at reduced pressure to yield a dark solid, which was stirred in 130 mL hexane and heated to reflux for one hour. Upon cooling to 20° C., the suspension was filtered to give a dark residue.

1.56 g of the dark residue was washed with 46.8 ml ethanol, and heated to reflux for one hour, and then cooled to 20° C., followed by filtered to yield a refined extract (766 mg). HPLC: 66.3%, indirubin, 9.76% indigo.

Example 7: Preparation of a Refined Indigo Naturalis Extract 500 g of Qingdai as described in Example 3 were suspended in 3 L DMF. The mixture was stirred at 30° C. for 1 hour, and then filtered. The filtrate was concentrated at reduced pressure to yield a dark solid, which was stirred in 230 mL hexane and heated to reflux for one hour. Upon cooling to 20° C., the suspension was filtered to give a dark residue.

1.96 g of the dark residue was washed with 59 mL 85% ethanol (85% aq. alcohol), and heated to reflux for one hour followed by filtration while hot to yield a refined extract (1.02 g). HPLC: 69.4% indirubin, 18.7% indigo, and 0.62% tryptanthrin.

Example 8: Preparation of a Refined Indigo Naturalis Extract 100 g of Qingdai was extracted with 2 L of ethanol 92% (92% aqueous ethanol) for 2 hours under reflux conditions. Upon completion, the mixture was filtered while hot on AF6 filter (Buchner) to obtain a dark blue-red solution as a filtrate. This filtrate was reduced under vacuum to dryness to give 2.4 g of dry residue. This residue was washed with 120 mL of hexane for 1 h under reflux. Upon completion, the mixture was cooled to room temperature for 2 h then filtered under vacuum to yield 312.9 mg of a dark red refined extract.

280 mg of this refined extract were washed with 15 mL of ethanol 92% (92% aqueous ethanol) for 1 h under reflux. Upon completion the solution was cooled to room temperature, and then filtered to yield 159 mg of a dark red/burgundy refined extract after drying in oven (80° C.) for 1 h30. (0.18%); HPLC: 82.31% indirubin, 8.99% indigo, and 0.81% tryptanthrin.

Example 9: Micronization Step of a Refined Indigo Naturalis Extract

The micronization step of refined Indigo Naturalis extract obtained in the previous examples is performed with the following equipment:

Micronizer: spiral jet Mill Diameter 200

Feeder: this equipment is used for the dosage of powder to feed the micronizer. The dosage is made thanks to two screws. This system allows a regularity of the flow.

Micronization consists to project grains of powder with jet of air. The contact of grains permits their explosion.

The following parameters of micronization are recorded during the micronization:

Ring pressure: 6 bar

Injector pressure: 3 bar

The flow of powder feed: 25 kg/h

The micronizer allows a cylindrical enclosure—holes around the enclosure for the injection of air.

Powder is introduced in the micronizer; grains are propelled thanks to jet of air. When grains have the desired size, they are concentrated in the center of the micronizer and they are breathed. To avoid any contamination by foreign particles or broken pieces of the equipment, an additional sieving (sieve: 700 µm) is performed.

The step is done manually after the micronization and before the packaging.

A granulometric analysis of the homogeneous product obtained was carried out according to the particular size distribution (PSD) method [Analytical specifications: D99≤30 µm].

B. Formulations Comprising a Refined Indigo Naturalis Extract

Example 10: Ointment Formulation

A refined Indigo Naturalis ointment formulation was prepared according to example 3A of the patent EP 2 489 358, from an olive oil extracted product of Indigo Naturalis

Example 11: Formulation A (Refined Indigo Naturalis Extract and Corticosteroid)

| Composition | % w/w |
|---|---|
| Olea Europaea (olive) fruit oil | 81.873 |
| Butylated hydroxytoluene (BHT) | 0.10 |
| Refined Indigo Naturalis extract* | 0.027 |
| Beeswax, white | 9 |
| White Petrolatum | 9 |
| Clobetasol dipropionate | 0.05 |

% are expressed in weight relative to the total weight of the composition.
*Refined Indigo Naturalis extract as described in one of examples 3-9

Manufacturing Process:
Step 1: Refined Indigo Naturalis extract, Clobetasol dipropionate, olive oil and BHT have been stirred and heated at 90° C. for at least 20 minutes in order to obtain a homogeneous preparation.
Step 2: Beeswax (white) and white petrolatum have been added at 90° C. and stirred at least 20 minutes until the mixture was homogeneous.
Step 3: The homogeneous mixture from step 2 has been cooled to 55° C. while stirring.
Step 4: The contents of step 3 have been maintained at 55° C. and the finished product has been filled into the packaging.

Example 12: Formulation B (Refined Indigo Naturalis Extract and Corticosteroid)

| Composition | % w/w |
|---|---|
| Olea Europaea (olive) fruit oil | 81.753 |
| Butylated hydroxytoluene (BHT) | 0.10 |
| Refined Indigo naturalis extract* | 0.027 |
| Beeswax, white | 9 |
| White Petrolatum | 9 |
| Betamethasone valerate (equivalent to 0.1% Betamethasone) | 0.12 |

% are expressed in weight relative to the total weight of the composition.
*Refined Indigo Naturalis extract as described in one of examples 3-9

Manufacturing Process:
Step 1: Refined Indigo Naturalis extract, Betamethasone valerate, olive oil and BHT have been stirred and heated at 90° C. for at least 20 minutes in order to obtain a homogeneous preparation.
Step 2: Beeswax (white) and white petrolatum have been added at 90° C. and stirred at least 20 minutes until the mixture was homogeneous.
Step 3: The homogeneous mixture from step 2 has been cooled to 55° C. while stirring.
Step 4: The contents of step 3 have been maintained at 55° C. and the finished product has been filled into the packaging.

Example 13: Formulation A (Indigo Naturalis Ointment)

| Phase | Composition | % w/w |
|---|---|---|
| A | Olea Europaea fruit oil (olive oil) | 81.873 |
| A | Butylated hydroxytoluene (BHT) | 0.10 |
| A | Refined Indigo Naturalis extract prepared according to example 8* | 0.027 |
| B | Beeswax, (white) | 9 |
| B | White Petrolatum | 9 |

*HPLC: 79.26% indirubin, 6.15% indigo, and 0.62% tryptanthrin.

Manufacturing Process:
Step 1: Refined Indigo Naturalis extract, olive oil and BHT have been stirred and heated at 90° C. for at least 20 minutes in order to obtain a homogeneous preparation. This mixture constituted phase A.
Step 2: Beeswax (white) and white petrolatum have been added to Phase A at 90° C. and stirred at least 20 minutes until the mixture was homogeneous.
Step 3: The homogeneous mixture from step 2 has been cooled to 55° C. while stirring.
Step 4: The contents of step 3 have been maintained at 55° C. and the finished product has been filled into the packaging.

Initial (T=0) specifications:

| | Time | | |
|---|---|---|---|
| Storage conditions | T 1 Month | T 2 Months | T 3 Months |
| RT (Room Temperature) | Complies with initial (T = 0) specification | | |
| 30° C. | Complies with initial (T = 0) specifications | | |
| 40° C. | Complies with initial (T = 0) specifications | | |

Chemical Stability:

The chemical stability of Indigo Naturalis Ointment has been evaluated by chemical assay of indirubine.

Indirubin is assayed in Indigo Naturalis Ointment using reverse phase high performance liquid chromatography (HPLC) and results are expressed as mg/g of indirubine in Indigo Naturalis Ointment.

| | Time | | | |
|---|---|---|---|---|
| Storage conditions | T0 | T 1 Month | T 2 Months | T 3 Months |
| | Indirubine (mg/g of ointment) | | | |
| 25° C. | 0.206 | 0.205 | 0.205 | 0.210 |
| 30° C. | — | 0.207 | 0.205 | 0.209 |
| 40° C. | — | 0.205 | 0.206 | 0.211 |

The results showed that the Indigo Naturalis ointment was physically and chemically stable for 3 months at RT, 30° C. and 40° C.

Chemical stability is defined as an assay value of ≥90% of T0 values.

Physical stability is defined as no significant change from initial observations.

Example 14: Formulation B

| Phase | Composition | % w/w |
|---|---|---|
| A | Caprylic/Capric Triglyceride | 69.973 |
| A | Refined Indigo Naturalis extract prepared according to example 8* | 0.027 |
| A | Glyceryl Dibehenate (and) Tribehenin (and) glyceryl behenate | 6 |
| A | Hydrogenated castor oil | 3 |
| A | Glyceryl stearate | 6 |
| B | PPG-15 stearyl ether | 15 |

*HPLC: 79.26% indirubin, 6.15% indigo, and 0.62% tryptanthrin.

Manufacturing Process:
Step 1: Refined Indigo Naturalis extract has been added to caprylic/capric triglyceride and has been heated to 90° C. and mixed for at least 20 minutes in order to obtain a homogeneous preparation.
Step 2: Glyceryl dibehenate (and) tribehenin (and) glyceryl behenate, hydrogenated castor oil, glyceryl stearate have been added to the contents of step 1. The mixture has been maintained at 90° C. and has been stirred for at least 10 minutes until homogeneous.
Step 3: The contents of step 2 (Phase A) has been cooled to 55° C. while stirring.
Step 4: Phase B (PPG-15 stearyl ether) has been added to Phase A at 55° C. while stirring for at least 10 minutes at 55° C. until homogeneous.
Step 5: Contents of step 4 have been cooled while stirring until the mixture reaches room temperature.

C. Clinical Trials

Example 15: Study Design

The objectives of the study is to evaluate the effect of Indigo Naturalis over 4 weeks (twice a day) in patients with Atopic Dermatitis.

The study is randomized, vehicle controlled, Investigator-blinded involving subjects with atopic dermatitis (AD) meeting specific inclusion/exclusion criteria.

Subjects with AD with IGA score of 2-3 (mild to moderate) and maximum total lesion body surface of 10% with at least one target plaque of AD of at least 20 cm$^2$ with similar severity on the body according to IGA score and meeting all inclusion criteria will be included in the study.

Each subject will apply study product on all AD lesions including one selected target lesion. Products will be applied twice daily following instructions given by the investigator
Efficacy Measurements
Clinical Evaluations
The following evaluations will be performed on only the selected target Lesion
Erythema
Erythema will be defined as abnormal redness of the skin and classified as follows:

| None | 0 | No erythema |
|---|---|---|
| Mild: | 1 | Faintly detectable erythema: very light pinkness |
| Moderate: | 2 | Dull red, clearly distinguishable |
| Severe: | 3 | Deep, dark red |

Papulation/Induration
Papulation/Induration will be defined as hardening or firmness of the tissue at, and around, the site of the lesions

| None | 0 | No papulation/induration |
|---|---|---|
| Mild | 1 | Barely perceptible elevation |
| Moderate | 2 | Clearly perceptible elevation but not extensive |
| Severe | 3 | Marked and extensive elevation |

Oozing/Crusting
Oozing/Crusting will be defined as a continuing process of exudation of fluid from the lesions/formation of scab-like material on the surface of lesions resulting from dried serum.

| None: | 0 | No oozing/crusting. |
|---|---|---|
| Mild: | 1 | Faint sign of oozing and/or weeping |
| Moderate: | 2 | Definite oozing |
| Severe: | 3 | Marked and extensive oozing/weeping; heavy crusting |

Excoriation
Excoriation will be defined as mechanical removal of epidermis via scratching.

| None: | 0 | No excoriation |
|---|---|---|
| Mild: | 1 | Scant evidence of excoriations with no signs of deeper skin damage (erosion, crust) |
| Moderate: | 2 | Several linear marks of skin with some showing evidence of deeper skin injury (erosion, crust) |
| Severe: | 3 | Many erosive or crusty lesions |

Lichenification
Lichenification will be defined as thickening of the skin with increased markings and hyperpigmentation.

| None: | 0 | No Lichenification |
|---|---|---|
| Mild: | 1 | Slight thickening of the skin discernible only by touch and with skin markings minimally exaggerated. |
| Moderate: | 2 | Definite thickening of the skin with skin markings exaggerated so that they form a visible criss-cross pattern. |
| Severe: | 3 | Thickened indurated skin with skin markings visibly portraying an exaggerated criss-cross pattern. |

Other Efficacy Measurements:
Investigator Global Assessment (IGA)

| Clear | 0 | No inflammatory signs of AD |
|---|---|---|
| Almost clear | 1 | Just perceptible erythema, and just perceptible papulation/infiltration |
| Mild disease | 2 | Mild erythema, and mild papulation/infiltration |
| Moderate disease | 3 | Moderate erythema, and moderate papulation/infiltration |
| Severe disease | 4 | Severe erythema, and severe papulation/infiltration |
| Very severe disease | 5 | Severe erythema, and severe papulation/infiltration with oozing/crusting |

Pruritus (NRS)

| None: | 0 | No itching |
|---|---|---|
| Mild: | 1 | Occasional, slight itching, not really bothersome |
| Moderate: | 2 | Constant or intermittent itching that is somewhat bothersome |
| Severe: | 3 | Intense itching that causes pronounced discomfort, disturbing normal activity |

The main secondary efficacy assessment utilized the Eczema Area and Severity Index (EASI) which incorporates severity of dermatitis and surface area involvement, with a possible score total ranging from 0 to 72.

Safety Assessment:

A safety assessment will be conducted for all subjects at baseline and every subsequent visit through collection of adverse events.

The safety parameters are:

Adverse event recording at each visit

Physical examination at Screening and Final visit

Principal Statistical Method:

TSS, each Individual score, their changes from Baseline, Change from baseline in IGA, Change from baseline in Pruritus score and Change from baseline in EASI, will be descriptively summarized by visit and by treatment received.

The bilateral differences between treatments will be analysed by a Wilcoxon rank sum test for all criteria except EASI. The bilateral differences between treatments in Change from baseline in EASI will be analysed by a Student t-test.

Proportion of patients with IGA at 0-1 at the end of treatment, proportion of patients with decrease in EASI score at the end of treatment will be descriptively summarized.

Time to partial clearing and to time to complete clearing will be calculated using the clearing score.

All tests will be two-sided and 0.05 will be used to declare significance.

Example 16: Report of Cases on Childrens

Five patients in this report were diagnosed by a dermatologist to have atopic dermatitis which meets the diagnostic criteria of Williams et al. (Williams H C, Burney P G J, Pembroke A C, Hay R J. The U.K. Working Party's Diagnostic Criteria for Atopic Dermatitis. III. Independent hospital validation. Br J Dermatol 1994; 131, 406-16). These patients had fluctuating AD which necessitated intermittent use of western medicine, such as corticosteroids, but they were apprehensive about the side effects.

Patient's ages ranged from 4 to 19 years old and all patients' AD were classified to be in the chronic stage with a severity level score of at least 3 (moderate disease) based on the Investigator's Global Assessment (IGA) (Table 1). (Eichenfield L F, Lucky A W, Boguniewicz M, Langley R G, Cherill R, et al. Safety and efficacy of pimecrolimus (ASM 981) cream 1% in the treatment of midl and moderate atopic dermatitis in children and adolescents. J Am Acad Dermatol. 2002; 46(4):495-504). All patients had a history of asthma or allergy rhinitis and an abnormal level of IgE (greater than 100).

Patients were instructed to apply oil extract of Indigo Naturalis in ointment, as described in Example 10, on to their skin lesions once or twice daily intensely for 3 to 8 weeks. Efficacy of the Indigo Naturalis extract in oil ointment was assessed by measuring the changes from baseline using Eczema Area and Severity Index (EASI) (Hanifin J M, Thurston M, Omoto M, Cherill R, Tofte S J, et al. The eczema area and severity index (EASI): assessment of reliability in atopic dermatitis. EASI Evaluator Group. Exp Dermatol. 2001; 10(1):11-8), body surface area (BSA) involvement, IGA and pruritus (10-cm visual analog scale). Based on the observations, this treatment method visibly improved their AD symptoms (Table 2). Patients reported no adverse side effects, even after continuing treatment for more than nine months.

TABLE 1

| | | Demographics | | |
|---|---|---|---|---|
| Patient | Age (yrs) | Gender | Age of onset (yrs) | IgE (IU/mL) |
| A | 19 | Female | 16 | 1,294 |
| B | 4 | Male | 1 | 150 |
| C | 18 | Male | 1 | >2,000 |
| D | 16 | Male | 4 | 646 |
| E | 6 | Female | 1 | 1,598 |

IGA: Investigator's Global Assessment

TABLE 2

Patient's Atopic Dermatitis Severity before and after treatment at week 6

| Patient | Treatment Duration (wks) | EASI Before | EASI After | EASI Change* | BSA (%) Before | BSA (%) After | Pruritus NSR Before | Pruritus NSR After | IGA Before | IGA After |
|---|---|---|---|---|---|---|---|---|---|---|
| A | 6 | 14.3 | 5.3 | 63% | 12 | 2.8 | 9 | 2 | 4 | 2 |
| B | 2 | 5.2 | 0.2 | 96% | 10 | 0.2 | 10 | 3 | 3 | 0 |
| C | 8 | 21.9 | 9.6 | 56% | 48 | 23 | 9 | 4 | 4 | 3 |
| D | 4 | 28.5 | 5.7 | 80% | 51 | 8 | 6 | 3 | 4 | 1 |
| E | 2 | 13.2 | 5.6 | 58% | 38 | 17.5 | 7 | 5 | 4 | 2 |

EASI: Eczema Area and Severity Index
BSA: Body Surface Area
IGA: Investigator's Global Assessment Patient A (FIG. 1) is a 19-year old female with a history of asthma and a 3-year history of AD. She suffered from severe itching with sleep loss, causing her to scratch her skin excessively, and her IgE level was high (1294). Her eczema lesions were located on her ocular area, neck, antecubital fossae, popliteal fossae and legs. She also had lichenoid desquamation eczema on her left forearm (FIG. 1C). After 6 weeks of intensive treatment, her dermatitis had a significant improvement (FIG. 1). Her EASI score and BSA improved 62.9% and 76.7%, respectively; and her pruritus also significantly decreased (Table 2). Her treatment was less consistent after 6 weeks; however, after 12 weeks of intermittent treatment her dermatitis was under control with less than 1% involvement of her body surface area. Due to her intermittent treatment, some of her prurigo lesions on her popliteal fossae remained after 9 months.

Patient B (FIG. 2) is a 4-year old male with a history of allergy rhinitis and food allergies including milk and sea food. He was diagnosed with AD when he was 1-year-old.

Figure 2:
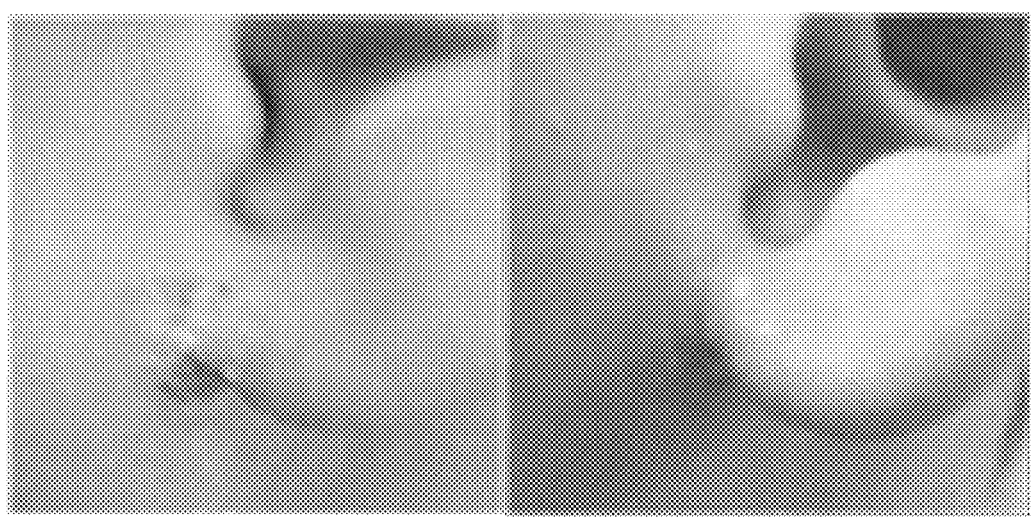
FIG. 2 Patient B—example 16—clinical improvement on the appearance of skin lesions after treatment with Indigo Naturalis extract ointment, as described in Example 10. Photos of the left ear lobe (A) left arm antecubital fossae (B) taken at baseline and week 2.
Figure 2:

He suffered from generalized skin dryness with excoriation and sleep loss due to severe itching. This patient had an elevated level of total IgE (150). His excoriated lesions were on the cheeks, ear lobes, antecubital fossae, on the back of the neck and thigh. After 2 weeks of treatment, his sleep had improved and no new lesions were noted (FIG. 2). His EASI score and BSA improved 96% and 98%, respectively (Table 2) Due to the fact that his skin lesions were nearly clear, the patient did not return for follow-up treatment after 3 weeks.

Figure 3:
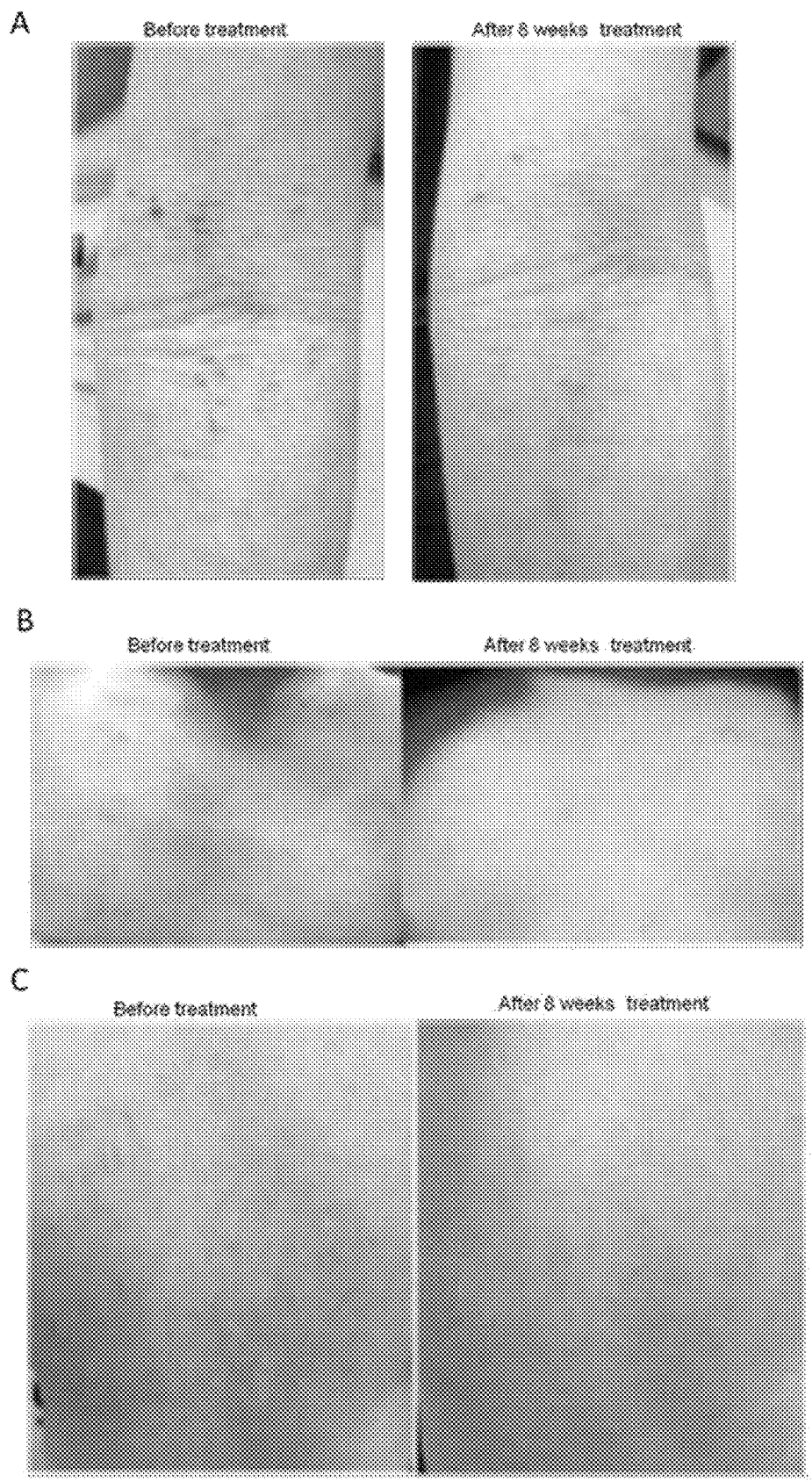
FIG. 3 Patient C—example 16—clinical improvement on the appearance of skin lesions after treatment with Indigo Naturalis extract ointment, as described in Example 10. Photos of the left arm antecubital fossae (A), chest (B), and back (C) taken at baseline and week 8.

Patient C (FIG. 3) is an 18-year old male with a history of allergy rhinitis and has had AD for more than 16 years. This patient had an extremely high level of IgE (greater than 2000). He had generalized dermatitis with lichenification over the majority of his skin and, due to excessive scratching of his wounds, had significant scarring. He had markedly accentuated skin lines on his limbs and abdominal area. After 6 weeks of intensive treatment, there was less scratching of his lesions and fewer lesions (FIG. 3), however, his skin lines will remain markedly accentuated. His EASI score and BSA improved 56.2% and 52.0%, respectively (Table 2). After 6 weeks, his follow-up treatment was intermittent but, on subsequent visits, his condition had stabilized with only occasional flare-ups that were due to his inconsistent treatment.

Figure 4:
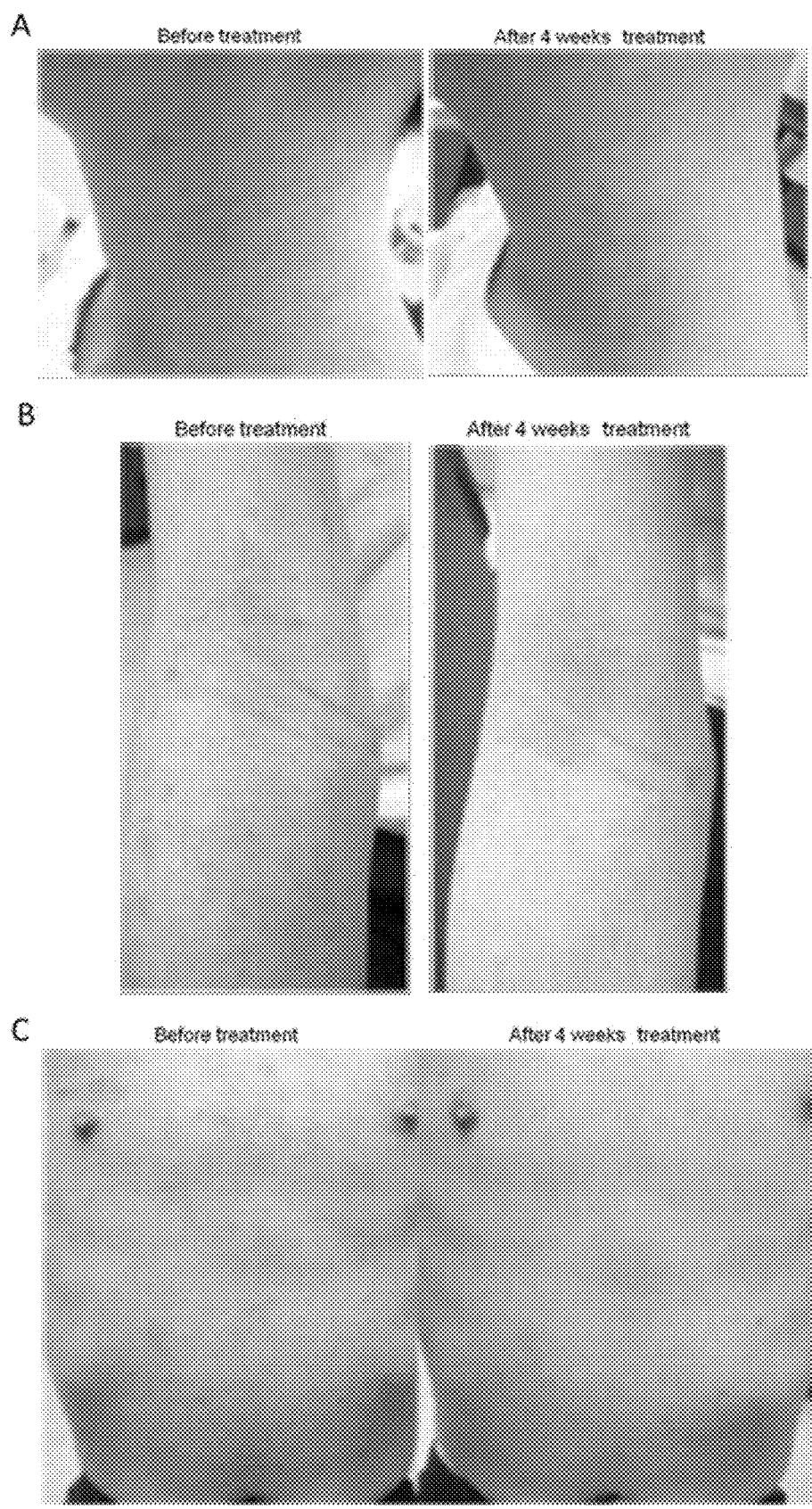
FIG. 4 Patient D—example 16—clinical improvement on the appearance of skin lesions after treatment with Indigo Naturalis extract ointment, as described in Example 10. Photos of the neck (A), right arm antecubital fossae (B), and trunk (C) taken at baseline and week 4.

Patient D is a 16-year old male with a history of allergy rhinitis and has had AD for more than 13 years. This patient also had a high level of total IgE (646). His dermatitis involved generalized skin desquamation and excoriation. The affected skin on the neck and forearm showed eczema with maculopapular rash and perifollicular accentuation. This patient had several lesions that had exudation with crust and folliculitis was also noted. After 4 weeks of intensive treatment, most of his lesions on the neck, arm and trunk had cleared including no desquamation (FIG. 4); however, lesions on his popliteal fossae remained. His EASI score and BSA improved 80% and 84.3%, respectively (Table 2). Due to the patient's improvement, he suspended his treatment; consequently, he returned for treatment after he had occasional flare-ups.

Figure 5:
FIG. 5 Patient E—example 16—clinical improvement on the appearance of skin lesions after treatment with Indigo Naturalis extract ointment, as described in Example 10. Photos of the back (A) and right arm antecubital fossae (B) taken at baseline and week 2.
Figure 5:
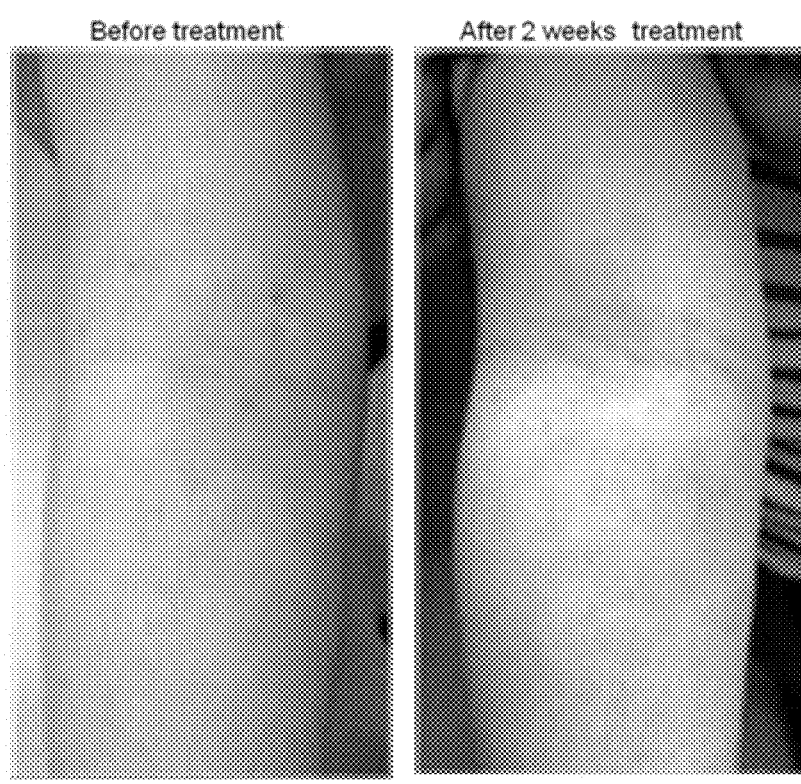
Figure 6:
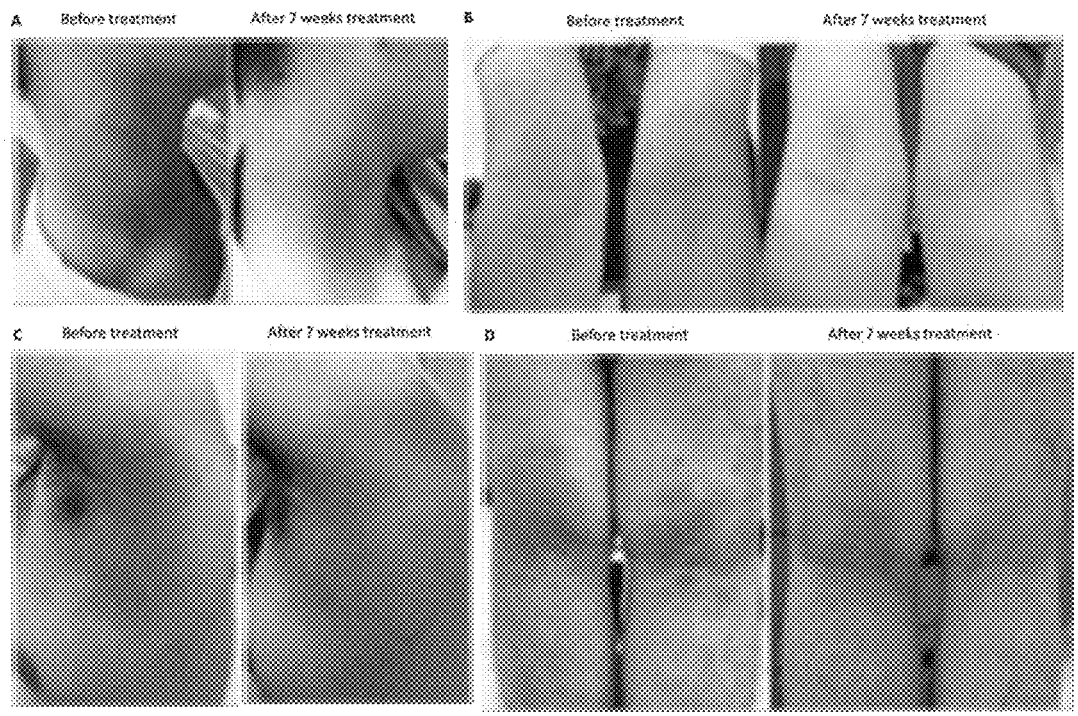
FIG. 6. Patient A—example 17—clinical improvement on the appearance of skin lesions after treatment with an Indigo Naturalis extract ointment, as described in Example 10. Photos of the right neck (A), antecubital fossae (B) left axilla (C) and popliteal fossae (D) taken at baseline and week 7.

Patient E is a 6-year old female with a history of allergy rhinitis and a 4-year history of AD. This patient also had an extremely high level of total IgE (1598). She suffered from severe generalized itching and desquamation, especially severe scratching lesions on her back. After 2 weeks of treatment, most of her scratching lesions were cleared but still had perceptible erythema and papulation (FIG. 5). Her EASI score and BSA improved 57.6% and 53.9%, respectively (Table 2). Although her excoriation and desquamation had significantly improved after 4 weeks of treatment, her skin itching was not under control and she did not return for follow-up treatment due to an upper respiratory infection.

In summary, the oil extract of Indigo Naturalis in ointment applied topically may have the potential to alleviate AD with no adverse side effects for long-term use. Such extract is an excellent choice for patients with chronic and stationary AD.

Example 17: Report of Cases on Adults

In this case series, four patients, 20 to 43 years old, were diagnosed with typical clinical AD skin features that have been diagnosed with AD since infancy or childhood (Table 3). All patients have a personal or family history of asthma, allergy rhinitis or food allergies. These patients have fluctuating AD and are worried about the long-term side effects from using topical corticosteroids or current systemic treatments. Patients were treated using the Indigo Naturalis extract ointment as described by example 10 to control their AD symptoms. This ointment was prepared and provided by the TCM pharmacy of Chang Gung Memorial Hospital in Taoyuan, Taiwan.

Patients were instructed to apply the ointment to their skin lesions at least twice daily and were closely monitored for 7 to 12 weeks, some continuing their treatment for several months afterward. Efficacy of the ointment in treating AD was assessed by measuring the change from baseline using the Eczema Area and Severity Index (EASI), Body Surface Area (BSA) involved with AD, Investigator's Global Assessment (IGA) and pruritus Numeric Rating Scale (NRS) (Table 4).

TABLE 3

Demographics

| Patient | Age (yrs) | Gender | Age of onset (yrs) | IgE (IU/mL) | Eosinophil count (%) |
| --- | --- | --- | --- | --- | --- |
| A | 25 | Male | 3 | unknown | 8.6 |
| B | 20 | Male | 0.4 | 1,180 | 8.5 |
| C | 43 | Male | 3 | 12,900 | 8.2 |
| D | 34 | Female | 4 | 25,000 | 13.6 |

IGA: Investigator's Global Assessment

TABLE 4

Patient's Atopic Dermatitis Severity

| Patient | Treatment Duration (wks) | EASI Before | EASI After | EASI Change* | BSA (%) Before | BSA (%) After | Pruritus NSR Before | Pruritus NSR After | IGA Before | IGA After |
| --- | --- | --- | --- | --- | --- | --- | --- | --- | --- | --- |
| A | 7 | 13.7 | 1.1 | 91.2% | 12 | 0.5 | 7 | 0 | 4 | 1 |
| B | 12 | 24 | 4 | 83.3% | 29 | 4.5 | 7 | 2 | 5 | 3 |
| C | 7 | 11 | 2.3 | 79.1% | 14 | 3 | 8 | 2 | 4 | 2 |
| D | 12 | 58.6 | 21.6 | 59.7% | 92 | 63 | 9 | 3 | 5 | 3 |

EASI: Eczema Area and Severity Index:
BSA: Body Surface Area:
Pruritus NSR: Pruritus Numeric Rating Scale:
IGA: Investigator's Global Assessment.
*The percentage of improvement compared to baseline Patient A is a 25-year old male who has a history of AD since he was 3 years old with generalized skin dryness and a history of food allergies. The patient's family history includes atopic eczema for his father and allergy rhinitis for his brother. On his first visit, he reported that he had eruptions for two weeks and was suffering from general skin itching. Confluent erythema, papules and scales were located on his neck, axilla, trunk, antecubital fossae, popliteal fossae and legs (FIGS. 6A-6D). He had generalized dryness of the skin and keratosis pilaris was also noted on the outside of his arms and upper thighs. In addition, he had acne on his face and back. He was treated at a local dermatology clinic with an unknown topical medicine but it failed to control his AD. On his initial visit, his EASI score was 13.7, BSA involved with AD was 12%, pruritus NRS was 7 and IGA score was 4 (Table 4). His blood test revealed an abnormal eosinophil count of 8.6% (reference range 0-5% for normal) but his IgE was not measured. After only two weeks of treatment with the ointment, his skin lesions showed dramatic improvement with the lesions on his axilla, trunk and antecubital fossae being almost clear and his EASI score improved to 2.3. After 7 weeks of treatment, the majority of the patient's lesions were almost clear with only a slight amount of papulation remaining on the right side of his neck and on his right antecubital fossae (FIGS. 6A-6D). His EASI score improved to 1.1, BSA involved with AD improved to 0.5%, pruritus NRS improved to 0 and IGA score improved to 1 (Table 4). In addition, his keratosis pilaris also showed slight improvement. Due to the fact that his skin lesions were almost clear, the patient did not return for follow-up after 7 weeks of treatment. Based on a telephone interview with the patient, he reported that his treatment with the ointment was less consistent but his AD was under control with no flare-ups for the past 5 months.

Figure 7:
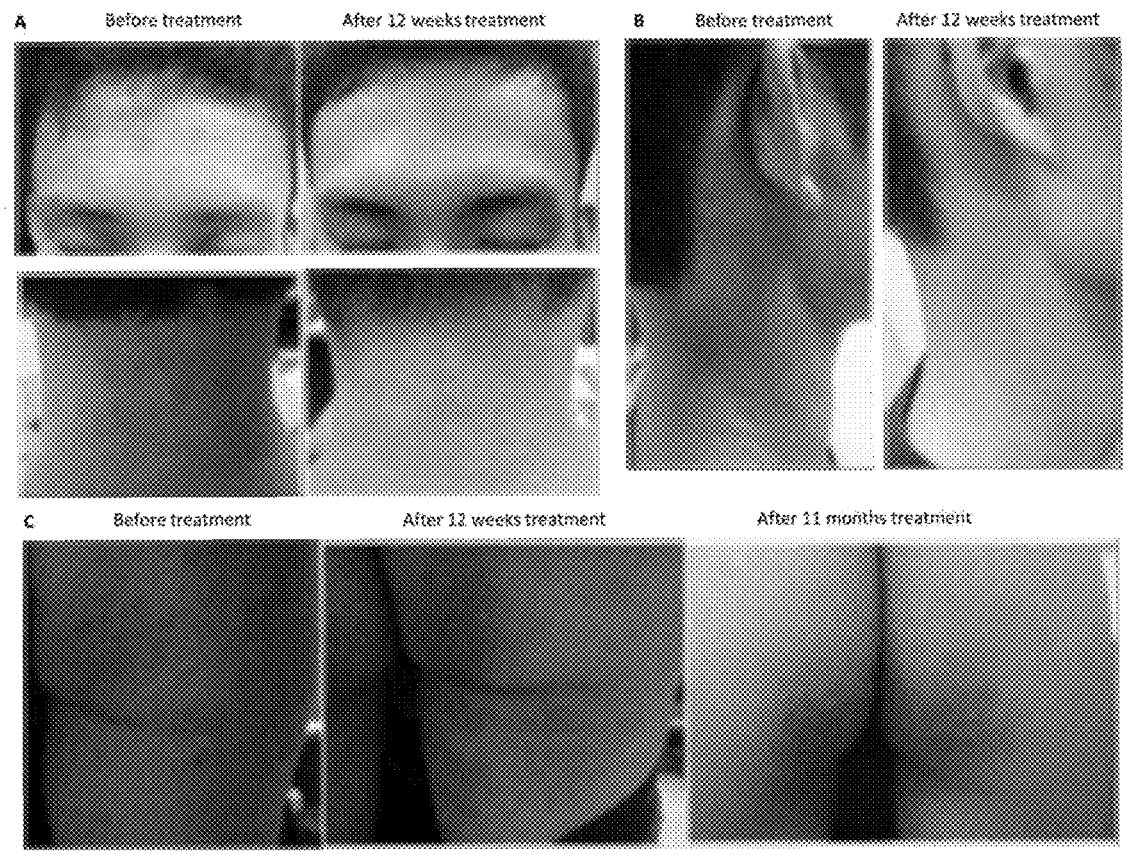
FIG. 7. Patient B—example 17—clinical improvement on the appearance of skin lesions after treatment with an Indigo Naturalis extract ointment, as described in Example 10. Photos of the forehead and neck (A), around ear and hairline (B), and buttock (C) taken at baseline, week 12 and month 11.

Patient B is a 20-year old male with a family history of allergy rhinitis and eczema. He experienced a brief AD attack at 5 months old but his AD went into remission until he was 12 years old. He had allergy rhinitis and asthma since infancy but they gradually improved through adolescence. He had intermittent AD flare ups after he was 12 years old that was treated using topical corticosteroids. His parents are afraid of the long-term adverse side effects from using corticosteroids, therefore, they switched his treatment to other systemic herbs at a local clinic but they were not effective in controlling his AD. On his initial visit, he had generalized skin dryness and keratosis pilaris noted on his neck and limbs. His AD was involved over the majority of his body characterized by confluent erythema, thickened papules and plaques, lichenification and excoriation. The most prominent erythematosus lesions with weeping, crusting and flaking were noted on his forehead, neck, around the ears and hairline (FIGS. 7A and 7B). His EASI score was 24, BSA involved with AD was 29%, pruritus NRS was 7 and IGA score was 5. His blood test showed an abnormal eosinophil count (8.5%) and an elevated level of IgE (1,180 IU/dL vs. reference range <100). After 12 weeks of intensive treatment, most of the lesions on his head, neck and arm were nearly cleared. Only hyperpigmented patches and lichenified plaques were present on his buttocks and popliteal fossae (FIG. 7C). His EASI score improved to 4, BSA involved with AD improved to 4.5%, pruritus NRS improved to 2 and IGA score improved to 3 (Table 4). The hyperpigmented patches and lichenified plaques on his buttocks and popliteal fossae showed significant improvement after 11 months of intermittent treatment (FIG. 7C). Following up after more than one year, his condition had stabilized and his skin was nearly cleared. He reported that he had occasional flare-ups on his neck, antecubital fossae and popliteal fossae that were most likely due to stress and his treatment being applied inconsistently.

Figure 8:
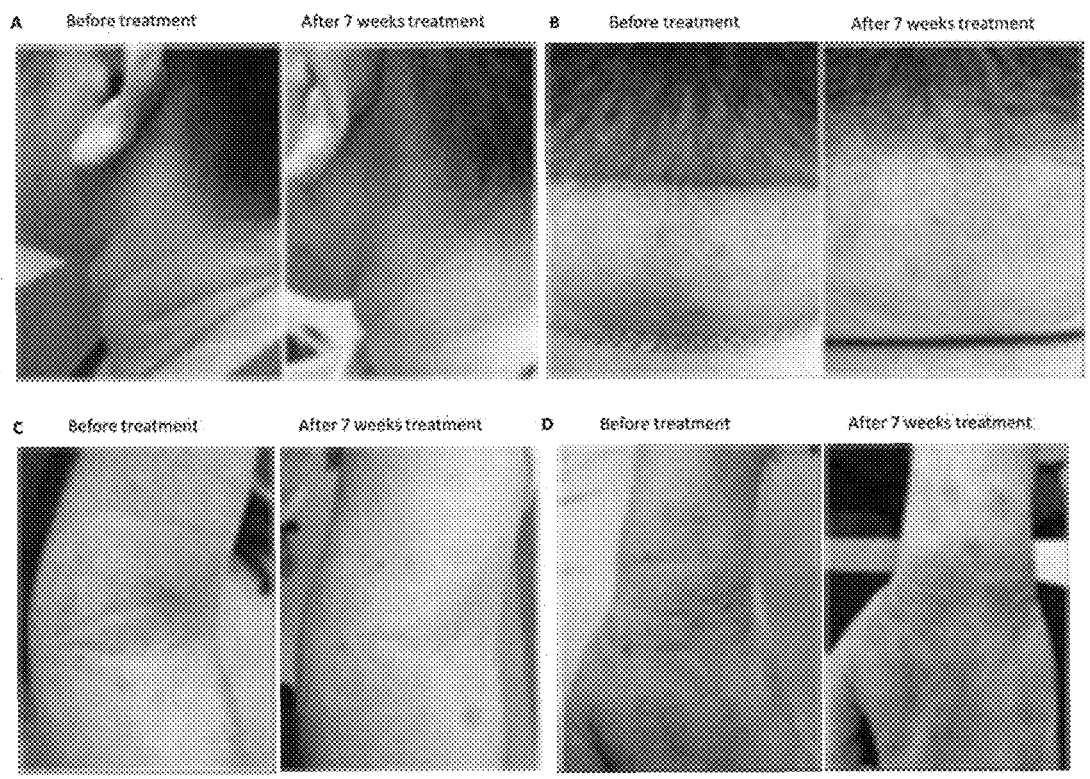
FIG. 8. Patient C—example 17—clinical improvement on the appearance of skin lesions after treatment with an Indigo Naturalis extract ointment, as described in Example 10. Photos of the left neck, around ear and hairline (A), poster neck (B), left antecubital fossae (C) and left dorsal hand (D) taken at baseline and week 7.

Patient C is a 43-year old male who was diagnosed with AD when he was around 3 years old and has a history of allergies to seafood. In the past, the patient treated his AD with topical corticosteroids and/or oral medicines but found that only corticosteroid injection treatment could control his AD. On his first visit, he was suffering from intense pruritus and confluent erythema with excoriation and scaling on his neck, eyelids, cheeks, ear lobes and occipital area (FIGS. 3A and 3B). His arms revealed severely flaking skin, prominent thickened papules and plaques with exaggerated skin markings (lichenification), erythema and excoriation. His antecubital fossae, dorsal hand and wrist had the most severe erythema, excoriation and lichenified plaques (FIGS. 8C and 8D). On his first visit, this patient's EASI score was 11, BSA involved with AD was 14%, pruritus NRS was 8 and IGA score was 4 (Table 4). His blood test revealed an abnormal eosinophil count (8.2%) and a high level of IgE (12,900 IU/dL). After only 3 weeks of treatment, the excoriation and confluent erythema on his neck were greatly reduced and the flaking of the skin was cleared. At week 7, the AD lesions on his face and neck were almost clear and the erythema, excoriation and lichenified plaques on his arms showed significant improvement (FIGS. 8A-8C). There were hyperpigmented, lichenified plaques and patches on his wrist and dorsal hands (FIG. 8D). His EASI score improved to 2.3, BSA involved with AD improved to 3%, pruritus NRS improved to 2 and IGA score improved to 2 (Table 4). The patient's skin condition continued to improve after 11 weeks, however, his AD flared up two months later due to complications from stress, a common cold and poor diet control. His AD is undergoing further treatment since the flare up.

Figure 9:
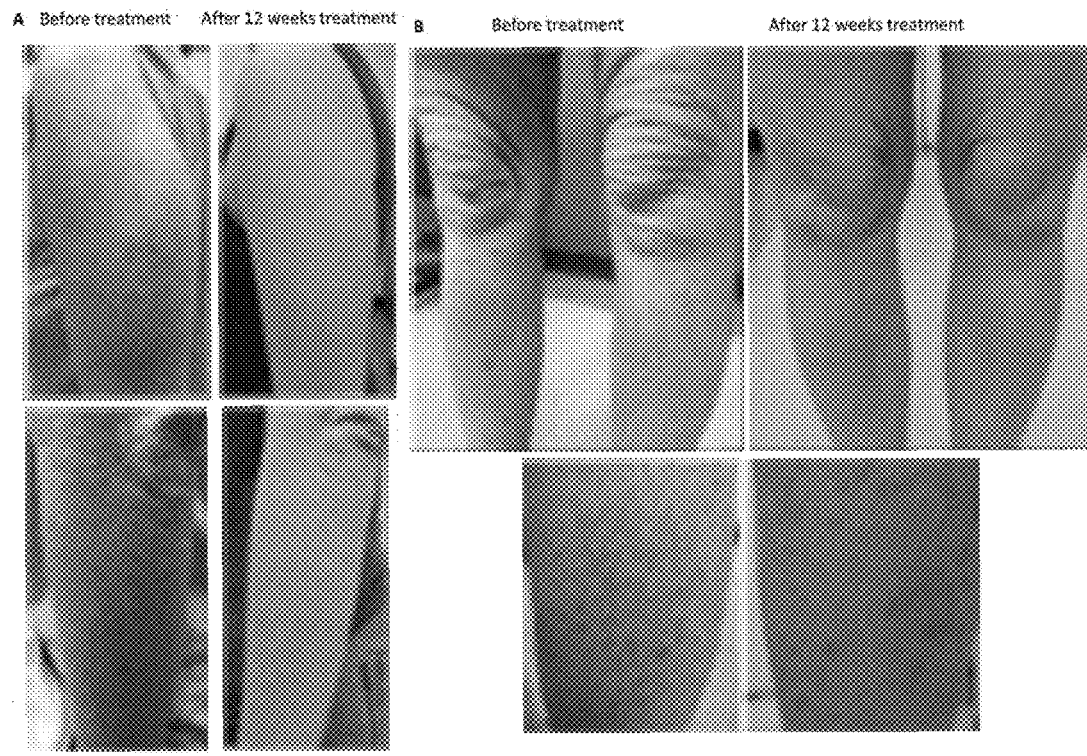
FIG. 9. Patient D—example 17—clinical improvement on the appearance of skin lesions after treatment with an Indigo Naturalis extract ointment, as described in Example 10. Photos of the forehead (A), and legs (B) taken at baseline and week 12.

Patient D is a 34-year old female with a history of asthma, food allergies (seafood, wheat and soy bean) and a family history of allergy rhinitis. She reported that her AD started when she was 4 years old and it became more severe after 11 years old involving generalized skin eruptions and excoriation with intense itching. In the past, she treated her AD with topical corticosteroids, systemic medicinal treatments and phototherapy but her AD rebounded after she discontinued her treatment. She tried various alternative treatments combined with topical moisturizers when she was 30 years old but they failed to control her AD. On her initial visit, her skin was generally inflamed with confluent erythema, thickened papules and plaques, cracking skin, flaking skin, and prominent skin thickening. She had exaggerated skin markings and deep furrows, especially above her knees (FIGS. 9A and 9B). She suffered from intense skin itching which caused scratching wounds resulting in some weeping and crusting from her lesions. Her EASI score was 58.6, BSA involved with AD was 92%, pruritus NRS was 9 and IGA score was 5 (Table 4). Her blood test showed a high eosinophil count (13.6%) and a very high level of IgE (25,000 IU/dL). After 12 weeks of intensive treatment, she reported that her skin itching had decreased significantly. Her scratching wounds had reduced and the scaling of the skin was nearly cleared. In addition, there was a significant reduction of inflamed skin, redness and skin thickening including a large reduction in the skin folds above her knees (FIGS. 9A and 9B). Her EASI score improved to 21.6, BSA involved with AD improved to 63%, pruritus NRS improved to 3 and IGA score improved to 3 (Table 4). Her AD flared up one month later due to a trip to Japan where she experienced cold weather and poor weather conditions and due to exposure to increased air pollution in Taiwan. However, her overall condition has greatly improved since her initial visit and she has been continuing her treatment intermittently to control her AD for the past three months and will continue her follow up treatment with our hospital.

Comments

In this AD case report, it can be observed that treatment with the extract of Indigo Naturalis can visibly improve AD symptoms in adults with very low therapeutic risks. Herein, this small case observational AD report showed that three out of four adult patients had achieved greater than 75% improvement in their EASI scores (Table 4) over 7 to 12 weeks of treatment. The ointment has been reported to be safe for up to two years of use with no adverse side effects in most cases.

Interestingly, the younger patients (A and B) with a short-term history of AD showed a better response compared to the older patients (C and D) who had poor control of their AD over a long-term (>30 years) and also had high levels of IgE (>10,000). Among the four patients, patient A had a very short history of flare ups and had the best response to treatment. Patient D has severe, refractory AD with a very high level of IgE (25,000) and a high eosinophil count (13.6%); therefore, her response to treatment was not as significant and will require more intensive treatment over time. Although improvements in AD were noted for most cases in this short-term observation, the more severe AD symptoms such as thickened papules, plaques and lichenification will need consistent, long-term treatment using the ointment to improve skin lesions to near normal condition (patient B, FIG. 7C).

Currently, AD cannot be cured and follows a chronic relapsing course over months to years. Patients with mild AD may experience intermittent flare-ups with spontaneous remission, but patients with moderate to severe AD rarely clear without treatment. It is important for most patients with AD to manage their AD symptoms and achieve long-term disease control by following careful skin care practice, using topical therapies for inflammation and by eliminating exacerbation factors. Besides effective treatment with medicines, it is necessary to reduce the factors which provoke flare-ups including: adhering to the treatment, avoiding poor external environments, reducing stress, avoiding contact allergens and avoiding foods that cause allergies.

In this report, patients B, C and D who had moderate-to-very-severe AD used various unproven treatments and used them inconsistently, resulting in poor control of their AD. All of these patients showed improvement in their AD after consistently following their treatment with the ointment. Patient B improved his AD by adhering to the treatment for more than one year and avoiding provoking factors, resulting in very obvious improvements in the lichenification of the lesions on his buttocks and popliteal fossae which are areas that are very difficult to treat (FIG. 7C). Patients C and D improved their AD in the first weeks, however, their AD digressed due to the effects of provoking factors.

The invention claimed is:

1. A method of treating an atopic dermatitis, comprising administering to a subject in need thereof a pharmaceutical composition comprising a solid extract of Indigo Naturalis and a pharmaceutically acceptable carrier,
wherein the solid extract comprises, relative to the total weight of the extract:
65% to 90% (w/w) indirubin;
0.1-15% (w/w) indigo; and
0.01-5% (w/w) at least one of tryptanthrin and qingdainone.

2. The method of claim 1, wherein the pharmaceutical composition comprises 0.01 to 10 mg of the solid extract of Indigo Naturalis per 1 g of the pharmaceutical composition.

3. The method of claim 1, wherein the solid extract comprises 0.1-5% (w/w) tryptanthrin and 0.1-5% (w/w) qingdainone relative to the total weight of the extract.

4. The method of claim 1, wherein the solid extract is micronized and comprises particles having a particle size of 25 to 35 μm in 99% of the particles.

5. The method of claim 1, wherein the pharmaceutical composition is in the form for topical administration.

6. The method of claim 1, further comprising administering to the subject in need thereof at least one selected from the group consisting of a corticosteroid, a calcineurin inhibitor and a phosphodiesterase inhibitor.

7. The method of claim 1, wherein the pharmaceutical composition further comprises at least one selected from the group consisting of a corticosteroid, a calcineurin inhibitor and a phosphodiesterase inhibitor.

8. The method of claim 1, wherein the subject is 25 years old or younger.

9. A method of treating an atopic dermatitis, comprising topically administering to a subject in need thereof, once or twice daily, a pharmaceutical composition comprising a solid extract of Indigo Naturalis and a pharmaceutically acceptable carrier,
wherein the pharmaceutical composition comprises 0.01 to 10 mg of the solid extract per 1 g of the pharmaceutical composition, and
the solid extract comprises, relative to the total weight of the extract:
65% to 90% (w/w) indirubin;
0.1-15% (w/w) indigo; and
0.01-5% (w/w) at least one of tryptanthrin and qingdainone.

10. The method of claim 9, wherein the solid extract comprises 0.1-5% (w/w) tryptanthrin and 0.1-5% (w/w) qingdainone relative to the total weight of the extract.

11. The method of claim 9, wherein the solid extract is micronized and comprises particles having a particle size of 25 to 35 μm in 99% of the particles.

12. The method of claim 9, further comprising administering to the subject at least one selected from the group consisting of a corticosteroid, a calcineurin inhibitor and a phosphodiesterase inhibitor.

13. The method of claim 9, wherein the pharmaceutical composition further comprises at least one selected from the group consisting of a corticosteroid, a calcineurin inhibitor and a phosphodiesterase inhibitor.

14. The method of claim 9, wherein the subject is 25 years old or younger.

15. A method of treating an atopic dermatitis, comprising administering to a subject in need thereof a pharmaceutical composition comprising a solid extract of Indigo Naturalis and a pharmaceutically acceptable carrier,
wherein the solid extract is prepared from Indigo Naturalis by a process comprising:
a) extracting the Indigo Naturalis with a solvent to obtain a mixture of extraction, wherein the solvent is selected from the group consisting of dimethylformamide, ethyl acetate, ethanol, dimethylsulfoxide, dichloromethane, tetrahydrofuran, dimethylacetamide, acetone, 2-butanone, acetonitrile, isopropyl acetate, 2-methyl tetrahydrofuran, methyl tert-butyl ether, methanol, chloroform, terpene, water and a combination thereof,
b) filtering the mixture of extraction to obtain a filtrate,
c) concentrating the filtrate to obtain a crude extract,
d) mixing the crude extract with hexane or heptane to obtain a washing mixture, and
e) filtering the washing mixture to obtain the solid extract.

16. The method of claim 15, wherein the solvent used in a) is selected from the group consisting of dimethylformamide, ethyl acetate, ethanol, and a combination thereof, or an aqueous solution thereof.

17. The method of claim 16, wherein in d), the crude extract is mixed with hexane or heptane at a temperature not less than 50° C. to obtain the washing mixture.

18. The method of claim 17, wherein in e), the washing mixture is cooled and filtered at room temperature to obtain the solid extract.

19. The method of claim 15, wherein the solid extract is prepared from Indigo Naturalis by the process comprising:
  a) extracting the Indigo Naturalis with a solvent to obtain a mixture of extraction, wherein the solvent is selected from the group consisting of ethyl acetate, ethanol, an aqueous solution of ethanol, and a combination thereof, and the mixture of extraction is obtained by mixing the Indigo Naturalis and the solvent in reflux,
  b) filtering the mixture of extraction at a temperature of not less than 65° C. to obtain a filtrate,
  c) concentrating the filtrate to obtain a crude extract,
  d) mixing the crude extract and hexane in reflux to obtain a first washing mixture,
  e) cooling and filtering the first washing mixture at room temperature to obtain a first extract product, and
  f) washing the first extract product with a washing method comprising:
    a) mixing the first extract product and a solvent selected from the group consisting of hexane, ethanol and an aqueous solution of ethanol in reflux to obtain a second washing mixture,
    b) cooling and filtering the second washing mixture at room temperature to obtain a second extract product, and
    c) drying the second extract product at a temperature of less than 80° C. to obtain a dried extract product,
  g) optionally washing the dried extract product with the washing method of f) one or more times to thereby obtain the solid extract.

20. The method of claim 19, wherein the process further comprises micronizing the solid extract.

\* \* \* \* \*